United States Patent
Ravi et al.

(10) Patent No.: US 9,199,933 B2
(45) Date of Patent: Dec. 1, 2015

(54) PROCESS FOR PREPARATION OF (1S, 3S, 5S)-2-[(2S)-2-AMINO-2-(3-HYDROXY-I-ADAMANTYL) ACETYL]-2-AZABICYCLO [3.1.0] HEXANE-3-CARBONITRILE

(71) Applicant: Ramamohan Rao Davuluri, Hyderabad (IN)

(72) Inventors: Ponniah Ravi, Madurai (IN); Praveen Kumar Neela, Hyderabad (IN); Batthini Guruswamy, Hyderabad (IN); Sribashyam Ravikanth, Hyderabad (IN); Uppala Manikya Rao, Guntur (IN); Dongari Naresh, Kalakova (IN); Mogili Ravindar, Hyderabad (IN)

(73) Assignee: Ramamohan Rao Davuluri (IN)

( * ) Notice: Subject to any disclaimer, the term of this patent is extended or adjusted under 35 U.S.C. 154(b) by 0 days.

(21) Appl. No.: 14/404,686

(22) PCT Filed: Apr. 22, 2013

(86) PCT No.: PCT/IN2013/000267
§ 371 (c)(1),
(2) Date: Dec. 1, 2014

(87) PCT Pub. No.: WO2013/179297
PCT Pub. Date: Dec. 5, 2013

(65) Prior Publication Data
US 2015/0112084 A1    Apr. 23, 2015

(30) Foreign Application Priority Data

May 30, 2012    (IN) .............................. 2172/CHE/2012

(51) Int. Cl.
| | | |
|---|---|---|
| *C07D 209/52* | (2006.01) | |
| *C07C 227/10* | (2006.01) | |
| *C07C 227/16* | (2006.01) | |
| *C07C 229/28* | (2006.01) | |
| *C07C 247/12* | (2006.01) | |

(52) U.S. Cl.
CPC ............ *C07D 209/52* (2013.01); *C07C 227/10* (2013.01); *C07C 227/16* (2013.01); *C07C 229/28* (2013.01); *C07C 247/12* (2013.01)

(58) Field of Classification Search
CPC ..................................................... C07D 209/52
See application file for complete search history.

(56) References Cited

U.S. PATENT DOCUMENTS

2005/0222242 A1*  10/2005  Sharma et al. ................ 514/412

* cited by examiner

*Primary Examiner* — Robert Havlin
(74) *Attorney, Agent, or Firm* — Schmeiser, Olsen & Watts, LLP

(57) ABSTRACT

Provided are novel processes for the preparation of Saxagliptin and novel intermediates employed in the process for preparing Saxagliptin.

15 Claims, No Drawings

PROCESS FOR PREPARATION OF (1S, 3S, 5S)-2-[(2S)-2-AMINO-2-(3-HYDROXY-1-ADAMANTYL) ACETYL]-2-AZABICYCLO [3.1.0] HEXANE-3-CARBONITRILE

CROSS REFERENCE TO RELATED APPLICATION

This application claims priority from the provisional specification No. 2172/CHE/2012 filed on 30 May 2012.

FIELD OF THE INVENTION

The present invention relates to novel processes for the preparation of Saxagliptin or its novel intermediates employed in the process for preparing Saxagliptin.

BACKGROUND OF THE INVENTION

Saxagliptin is chemically known as (1S3S,5S)-2-[(2S)-2-amino-2-(3-hydroxy-1-adamantyl) acetyl]-2-azabicyclo [3.1.0]hexane-3-carbonitrile having the chemical formula Saxagliptin is marketed under the trade name Onglyza by Bristol-Myers Squibb for the treatment of Type-2 diabetes.

Saxagliptin or its pharmaceutically acceptable salts were first disclosed in the U.S. Pat. No. 6,395,767 (herein after referred as U.S. '767) by Bristol-Myers Squibb in the Example 60. The patent U.S. '767 discloses the process for the preparation of Saxagliptin as depicted in the Scheme I:

Scheme - I

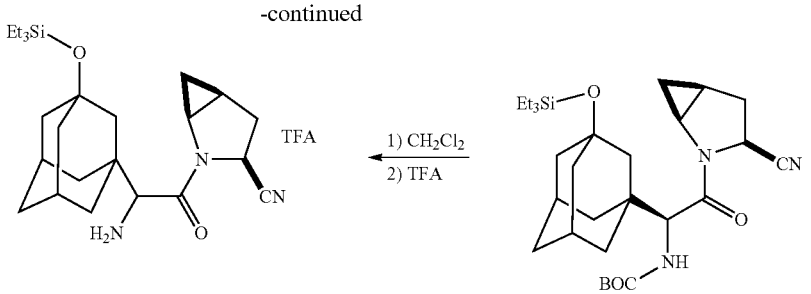

The aforementioned Scheme for preparing Saxagliptin employs lithium aluminum hydrate pyrophoric solvents and harmful reagents like potassium cyanide whose usage are not affordable in commercial process. These reagents are not environment friendly and the process is not commercially suitable for the preparation of Saxagliptin in large scale.

The patents U.S. Pat. No. 7,420,079, U.S. Pat. No. 7,186,846 and U.S. Pat. No. 7,205,432 disclose the process for the preparation of Saxagliptin overcoming the disadvantages of U.S. '767. Therefore, there exists a need for a novel, environment friendly, efficient and commercially viable process for the preparation of Saxagliptin.

SUMMARY OF THE INVENTION

The present invention provides novel processes for the preparation of Saxagliptin and novel intermediates employed in the process for preparing Saxagliptin.

It is an object of the present invention to provide a novel process for preparing Saxagliptin which comprises the steps of:

i) reacting the compound of formula III or its acid addition salts,

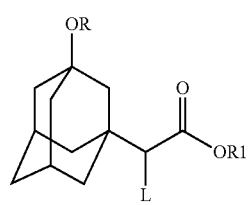

Formula III where in R and R1 independently is H or C1-C6 substituted or unsubstituted alkyl group; L is a halogen or leaving group; with alkali metal azide in the presence of a phase transfer catalyst to obtain a compound of formula IV or its acid addition salt thereof,

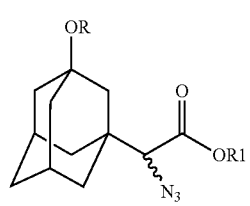

Formula IV wherein R and R1 independently is H or C1-C6 substituted or unsubstituted alkyl group;

ii) reacting the compound of formula IV with the compound 2-azabicyclo[3.1.0]hexane-3-carboxamide of formula VII or its acid addition salts,

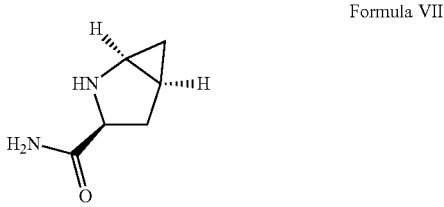

Formula VII in the presence of a coupling reagent and coupling additives to obtain a compound of formula VIII or its acid addition salts;

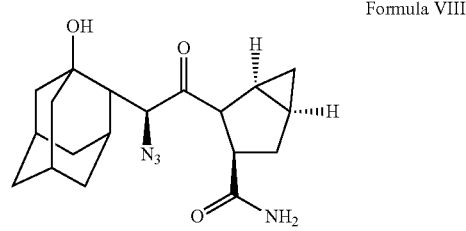 [SMILES: [N-]=[N+]=N[C@H](C(=O)C1[C@H]2C[C@H]2C[C@H]1C(N)=O)C1C2CC3CC(C2)CC1(O)C3]

Formula VIII iii) dehydrating the compound of formula VIII in the presence of a dehydrating reagent and base to obtain a compound of formula IX or its acid addition salts;

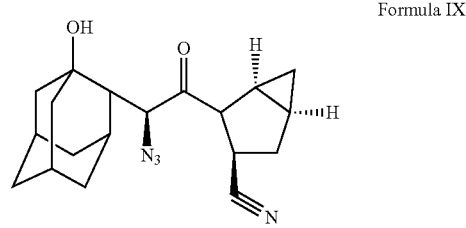 [SMILES: N#C[C@@H]1C[C@@H]2C[C@@H]2C1C(=O)[C@@H](N=[N+]=[N-])C1C2CC3CC(C2)CC1(O)C3]

Formula IX iv) reducing the compound of formula IX in the presence of a metal catalyst to obtain compound of formula X or its acid addition salts.

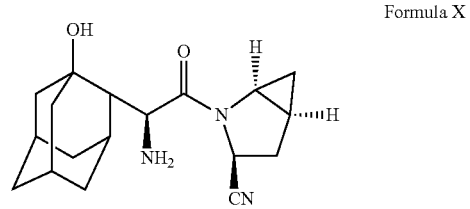 [SMILES: N#C[C@@H]1C[C@@H]2C[C@@H]2N1C(=O)[C@@H](N)C1C2CC3CC(C2)CC1(O)C3]

Formula X

It is another object of the present invention to provide a novel process for preparing Saxagliptin which comprises the steps of:

i) reacting the compound of formula III or its acid addition salts,

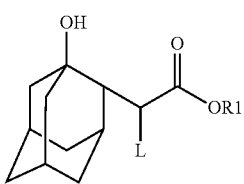

Formula III where in R and R1 independently is H or C1-C6 substituted or unsubstituted alkyl group; L is a halogen or leaving group; with alkali metal azide in the presence of a phase transfer catalyst to obtain a compound of formula IV or its acid addition salt thereof,

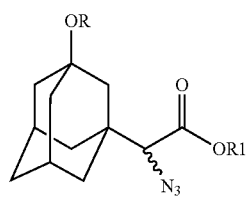

Formula IV wherein R and R1 is independently is H or C1-C6 substituted or unsubstituted alkyl group;

ii) treating the compound of formula IV with chiral reagent to obtain the compound of formula V;

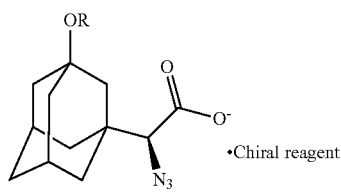

Formula V iii) hydrolysing of the compound of formula V by employing mineral acid to obtain a compound of formula VI or it acid addition salts,

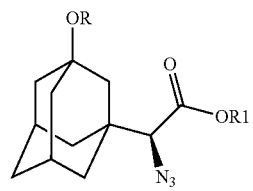

Formula VI wherein R and R1 independently is H or C1-C6 substituted or unsubstituted alkyl group;

iv) reacting the compound of formula VI or its acid addition salt with the compound 2-azabicyclo[3.1.0]hexane-3-carboxamide of formula VII or its acid addition salts,

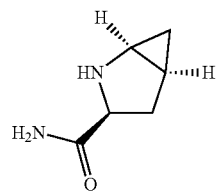

Formula VII in the presence of a coupling reagent and coupling additives to obtain a compound of formula VIII or its acid addition salts;

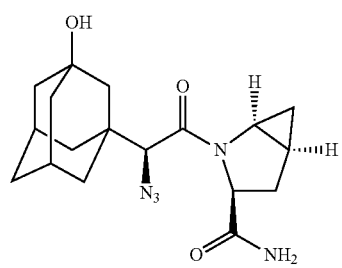

Formula VIII v) dehydrating the compound of formula VIII or its acid addition salts in the presence of a dehydrating reagent and a base to obtain a compound of formula IX or its acid addition salts;

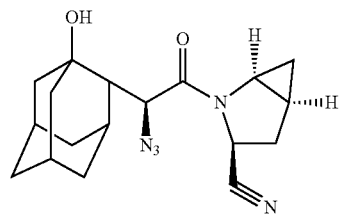

Formula IX vi) reducing the compound of formula IX or its acid addition salts in the presence of a metal catalyst to obtain compound of formula X or its acid addition salts.

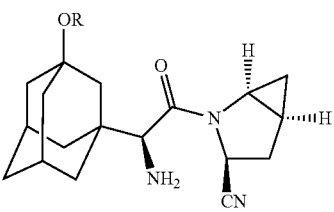

Formula X

It is yet another object of the present invention to provide a novel process for preparing Saxagliptin comprising the steps of:

i) reacting the compound of the formula III or its acid addition salts,

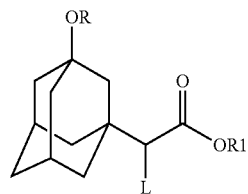
Formula III where in R and R1 independently is H or C1-C6 substituted or unsubstituted alkyl group; L is a halogen or leaving group; with PhCH$_2$NH$_2$ to obtain a compound of formula IVa or its acid addition salts,

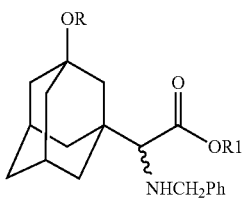
Formula IVa wherein Ph is unsubstituted or substituted aryl group;
ii) treating the compound of formula IVa with chiral reagent to obtain a compound of formula Va;

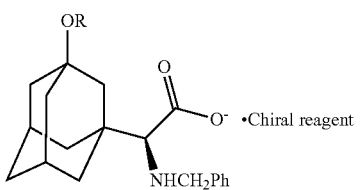
Formula Va iii) hydrolysis the compound of formula Va in the presence of mineral acid to obtain a compound of formula VIa or its acid addition salts;

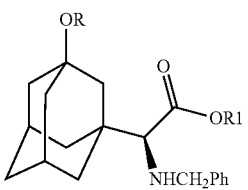
Formula VIa iv) reacting the compound of formula VIa with the compound 2-azabicyclo[3.1.0]hexane-3-carboxamide of formula VII or its acid addition salts,

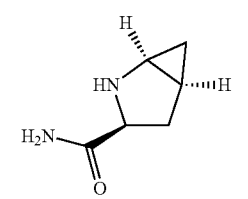
Formula VII in the presence of a coupling reagent and coupling additive to obtain a compound of formula VIIIa or its acid addition salts;

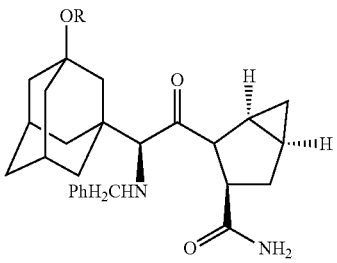
Formula VIIIa v) treating the compound of formula VIIIa or its acid addition salts with dehydrating agent in the presence of a base to obtain a compound of formula IXa or its acid addition salts;

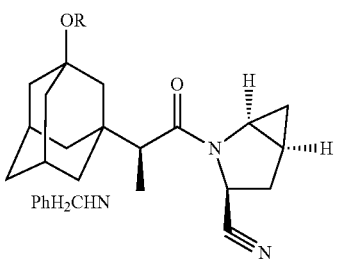
Formula IXa vi) catalytically reducing the compound of formula IXa or its acid addition salts in the presence of metal catalyst to obtain the compound of formula X or its acid addition salts.

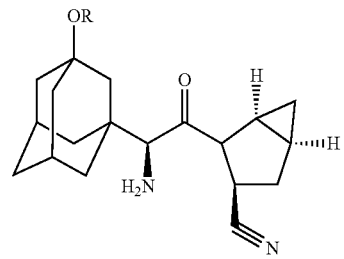
Formula X

It is yet another object of the present invention to provide a process for the preparation of Saxagliptin comprising the steps of:
i) treating the compound of formula VIII or its acid addition salts

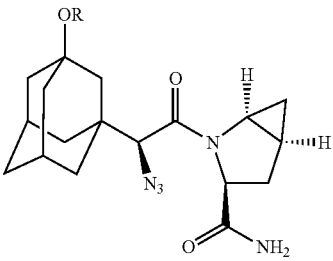
Formula VIII with palladium catalyst to obtain the compound of formula A or its acid addition salts;

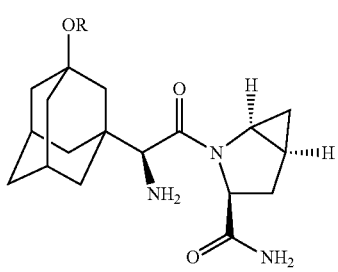

Formula A ii) treating the formula A or its acid addition salts with N-protecting reagents to obtain the compound of formula B or its acid addition salts,

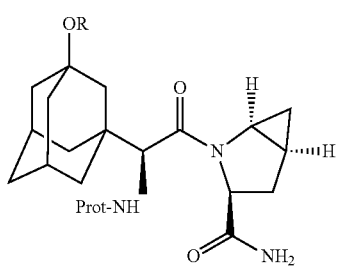

Formula B wherein Prot is N-protecting group;

iii) treating the compound of formula B or its acid addition salts with dehydrating reagent and base to obtain a compound of formula C or its acid addition salts;

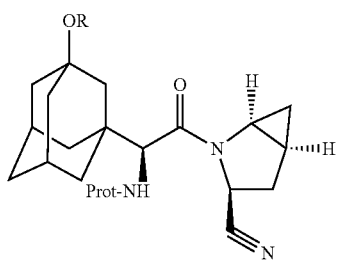

Formula C iv) treating the compound of formula C or its acid addition salts with mineral acid to obtain Saxagliptin or its acid addition salts.

DESCRIPTION OF THE INVENTION

The present invention involves novel processes for the preparation of Saxagliptin or its acid addition salts by employing novel intermediates.

In the first embodiment of the present invention a novel process for preparing Saxagliptin is provided which comprises the steps of:

i) reacting the compound of formula III or its acid addition salts,

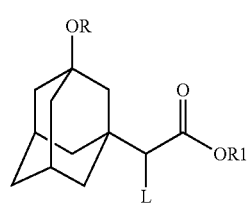

Formula III wherein R and R1 independently is H or C1-C6 substituted or unsubstituted alkyl group; L is a halogen or leaving group; with alkali metal azide in the presence of a phase transfer catalyst to obtain a compound of formula IV or its acid addition salt thereof,

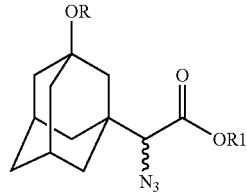

Formula IV wherein R and R1 independently is H or C1-C6 substituted or unsubstituted alkyl group;

ii) reacting the compound of formula IV with the compound 2-azabicyclo[3.1.0]hexane-3-carboxamide of formula VII or its acid addition salts,

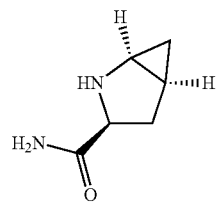

Formula VII in the presence of a coupling reagent and coupling additives to obtain a compound of formula VIII or its acid addition salts;

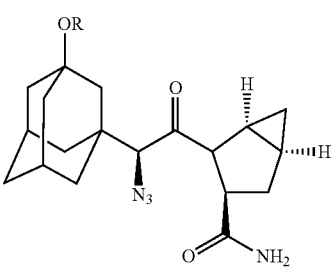

Formula VIII iii) dehydrating the compound of formula VIII or its acid addition salts in the presence of a dehydrating reagent and base to obtain a compound of formula IX or its acid addition salts;

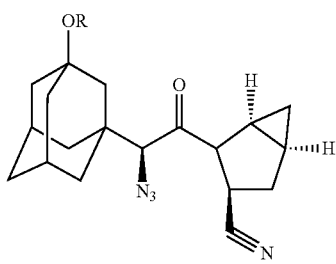

Formula IX iv) reducing the compound of formula IX or its acid addition salts in the presence of a metal catalyst to obtain compound of formula X or its acid addition salts.

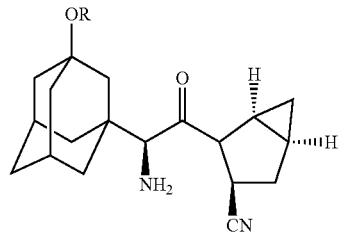

Formula X

The alkali metal azide employed in the step i) is selected from the group consisting of sodium azide, potassium azide, rubidium azide and cesium azide.

The phase transfer catalyst employed in the step i) is selected from the group consisting of tetrabutyl ammonium chloride and tetrabutyl ammonium hydrogen sulphate.

The coupling reagent employed in step ii) is selected from the group of 1-ethyl-3-(3-dimethylaminopropyl) carbodiimide) HCl, N,N'-Dicyclohexylcarbodiimide, N,N,N',N'-Tetramethyl-O-(benzotriazol-1-yl)uronium tetrafluoroborate, O-(6-Chloro-1-hydrocibenzotriazol-1-yl)-1,1,3,3-tetra methyluronium tetrafluoroborate and benzotriazol-1-yl-oxytripyrrolidinophosphonium hexafluoro phosphate.

The coupling additives employed in step ii) is selected from the group of hydroxybenzotriazole, hydroxybenzotriazole chloride and 1-hydroxy-7-azabenzotriazole.

The dehydrating reagent employed in step iii) is selected from the group of trifluoro acetic anhydride, acetic anhydride, p-toulenesulfonyl chloride and bezenesulfonyl chloride trifluoro acetic anhydride.

The base employed in step iii) is selected from the group of organic bases such as triethylamine, disopropylethylamine, pyridine, 2,6-dimethyl pyridine triethylamine and inorganic bases such as sodium hydroxide, potassium hydroxide, ammonium hydroxide, sodium bicarbonate, potassium bicarbonate, ammonium bicarbonate.

The metal catalyst employed in step iv) is selected from the group of Zn, Pt, Pd, Ni, Fe.

Suitable organic solvents employed to carry out the process included but are not limited to: alcohols such as methanol, ethanol, isopropyl alcohol, isobutyl alcohol, tertiary-butyl alcohol and the like; halogenated hydrocarbons such as dichloromethane, ethylene dichloride, chloroform and the like; ketones such as acetone, methyl isobutyl ketone and the like; nitriles such as acetonitrile, propionitrile and the like; ethers such as dimethyl ether, diethyl ether, diisopropyl ether, tetrahydrofuran, methyl tertiary-butyl ether and the like; esters such as ethyl acetate, n-propyl acetate, isopropyl acetate, n-butyl acetate, isobutyl acetate and the like; hydrocarbons such as hexane, benzene, xylene, toluene and the like and aprotic polar solvents such as dimethyl sulfoxide, N,N-dimethylformamide, N,N-dimethylacetamide and the like. Any solvent or mixture of solvents or their combination with water or any of the solvents from the classes mentioned above is acceptable.

In the second embodiment of the present invention another novel process for preparing Saxagliptin is provided which comprises the steps of:

i) reacting the compound of formula III or its acid addition salts,

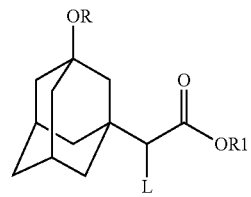

Formula III wherein R and R1 independently is H or C1-C6 substituted or unsubstituted alkyl group; L is a halogen or leaving group; with alkali metal azide in the presence of a phase transfer catalyst to obtain a compound of formula IV or its acid addition salts;

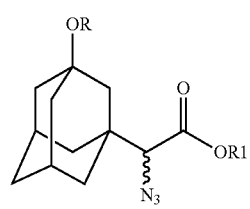

Formula IV wherein R and R1 independently is H or C1-C6 substituted or unsubstituted alkyl group;
ii) treating the compound of formula IV with chiral reagent to obtain a compound of formula V;

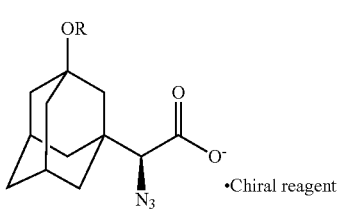

Formula V wherein R is substituted or unsubstituted alkyl, substituted or unsubstituted aryl group;
iii) hydrolysing the compound of formula V by employing mineral acid to obtain a compound of formula VI or its acid addition salts,

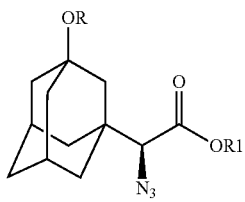
Formula VI wherein R and R1 independently is H or C1-C6 substituted or unsubstituted alkyl group;

iv) reacting the compound of formula VI or its acid addition salts with the compound 2-azabicyclo[3.1.0]hexane-3-carboxamide of formula VII or its acid addition salts;

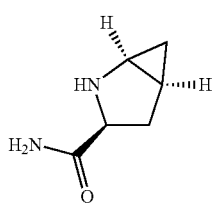
Formula VII in the presence of a coupling reagent and coupling additives to obtain a compound of formula VIII or its acid addition salts;

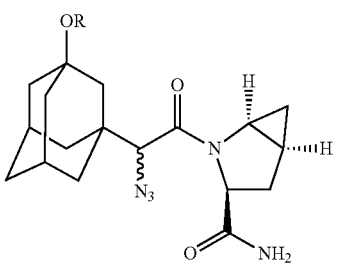
Formula VIII v) dehydrating the compound of formula VIII or its acid addition salts in the presence of a dehydrating reagent and base to obtain a compound of formula IX or its acid addition salts;

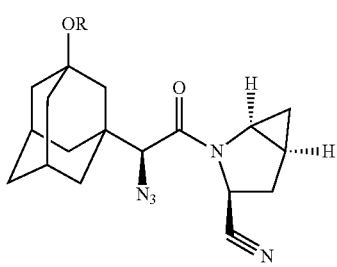
Formula IX vi) reducing the compound of formula IX or its acid addition salts in the presence of metal catalyst to obtain compound of formula X or its acid addition salts.

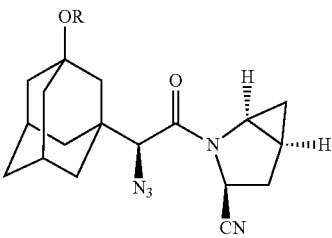
Formula X

The alkali metal azide employed in the step i) is selected from the group consisting of sodium azide, potassium azide, rubidium azide and cesium azide.

The phase transfer catalyst employed in the step i) is selected from the group consisting of tetrabutyl ammonium chloride and tetrabutyl ammonium hydrogen sulphate.

The chiral reagent employed in the step ii) is selected from the group of (S)-alpha methyl benzyl amine, (S)-phenyl ethyl amine, (S)-1,2 diamino propane, (S)-3-hydroxy pyrrolidine and (S)-phenyl alanine amide.

The coupling reagent employed in step iv) is selected from the group of 1-ethyl-3-(3-dimethylaminopropyl) carbodiimide) HCl, N,N'-Dicyclohexylcarbodiimide, N,N,N',N'-Tetramethyl-O-(benzotriazol-1-yl)uronium tetrafluoroborate, O-(6-Chloro-1-hydrocibenzotriazol-1-yl)-1,1,3,3-tetra methyluronium tetrafluoroborate and benzotriazol-1-yl-oxytripyrrolidinophosphonium hexafluoro phosphate.

The coupling additives employed in step iv) is selected from the group of hydroxybenzotriazole, hydroxybenzotriazole chloride and 1-hydroxy-7-azabenzotriazole.

The dehydrating reagent employed in step v) is selected from the group of trifluoro acetic anhydride, acetic anhydride, p-toulenesulfonyl chloride and bezenesulfonyl chloride trifluoro acetic anhydride.

The base employed in step v) is selected from the group of organic bases such as triethylamine, disopropylethylamine, pyridine, 2,6-dimethyl pyridine triethylamine and inorganic bases such as sodium hydroxide, potassium hydroxide, ammonium hydroxide, sodium bicarbonate, potassium bicarbonate, ammonium bicarbonate.

The metal catalyst employed in step vi) is selected from the group of Zn, Pt, Pd, Ni, Fe.

Suitable organic solvents employed to carry out the process included but are not limited to: alcohols such as methanol, ethanol, isopropyl alcohol, isobutyl alcohol, tertiary-butyl alcohol and the like; halogenated hydrocarbons such as dichloromethane, ethylene dichloride, chloroform and the like; ketones such as acetone, methyl isobutyl ketone and the like; nitriles such as acetonitrile, propionitrile and the like; ethers such as dimethyl ether, diethyl ether, diisopropyl ether, tetrahydrofuran, methyl tertiary-butyl ether and the like; esters such as ethyl acetate, n-propyl acetate, isopropyl acetate, n-butyl acetate, isobutyl acetate and the like; hydrocarbons such as hexane, benzene, xylene, toluene and the like and aprotic polar solvents such as dimethyl sulfoxide, N,N-dimethylformamide, N,N-dimethylacetamide and the like. Any solvent or mixture of solvents or their combination with water or any of the solvents from the classes mentioned above is acceptable.

In the third embodiment of the present invention another process for the preparation of Saxagliptin is provided comprising the steps of:

i) treating the compound of formula VIII or its acid addition salts,

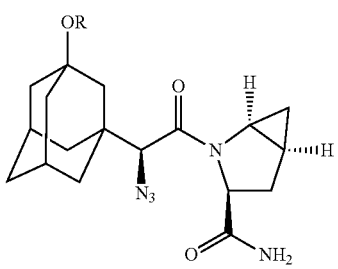

Formula VIII with palladium catalyst to obtain the compound of formula A or its acid addition salts;

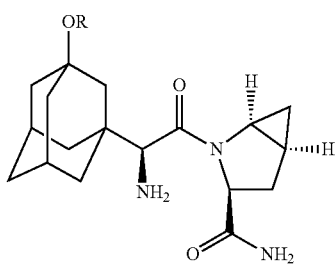

Formula A ii) treating the compound of formula A or its acid addition salts with N-protecting reagents to obtain the compound of formula B or its acid addition salts;

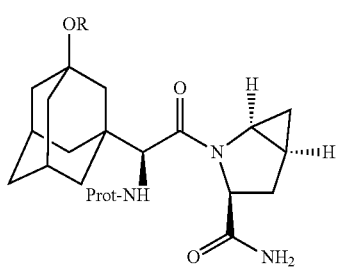

Formula B wherein Prot is N-protecting group;
iii) treating the compound of formula B or its acid addition salts with dehydrating reagent and base to obtain a compound of formula C or its acid addition salts;

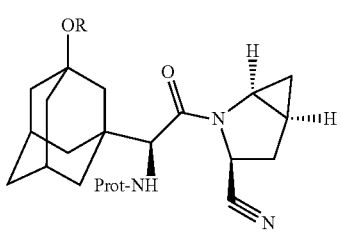

Formula C iv) treating the compound of formula C or its acid addition salts with mineral acid to obtain the Saxagliptin or its acid addition salts.

The N-protecting reagents employed in step ii) is selected from the group of carbobenzyloxy, p-methoxybenzyl carbonyl, tert-butyloxycarbonyl, 9-fluorenylmethyloxycarbonyl, benzoyl, benzyl, carbamate group, p-methoxybenzyl and 3,4-dimethoxybenzyl.

The dehydrating reagent employed in step iii) is selected from the group of trifluoroaceticannhydride, aceticannhydride, p-toulenesulfonyl chloride and bezenesulfonyl chloride.

The base is employed in step iii) is selected from the group of organic bases such as triethylamine, disopropylethylamine, pyridine, 2,6-dimethyl pyridine triethylamine and inorganic bases such as sodium hydroxide, potassium hydroxide, ammonium hydroxide, sodium bicarbonate, potassium bicarbonate, ammonium bicarbonate.

Suitable organic solvents employed to carry out the process included but are not limited to: alcohols such as methanol, ethanol, isopropyl alcohol, isobutyl alcohol, tertiary-butyl alcohol and the like; halogenated hydrocarbons such as dichloromethane, ethylene dichloride, chloroform and the like; ketones such as acetone, methyl isobutyl ketone and the like; nitriles such as acetonitrile, propionitrile and the like; ethers such as dimethyl ether, diethyl ether, diisopropyl ether, tetrahydrofuran, methyl tertiary-butyl ether and the like; esters such as ethyl acetate, n-propyl acetate, isopropyl acetate, n-butyl acetate, isobutyl acetate and the like; hydrocarbons such as hexane, benzene, xylene, toluene and the like and aprotic polar solvents such as dimethyl sulfoxide, N,N-dimethylformamide, N,N-dimethylacetamide and the like. Any solvent or mixture of solvents or their combination with water or any of the solvents from the classes mentioned above is acceptable.

In the fourth embodiment of the present invention another process for preparing Saxagliptin is provided which comprises the steps of:

i) reacting the compound of the formula III or its acid addition salts,

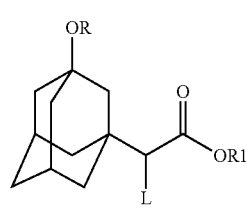

Formula III where in R and R1 independently is H or C1-C6 substituted or unsubstituted alkyl group; L is a halogen or leaving group;

with PhCH2NH2 to obtain a compound of formula IVa or its acid addition salts,

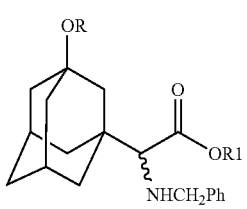

Formula IVa wherein Ph is unsubstituted or substituted aryl;

ii) treating the compound of formula IVa with a chiral reagent to obtain a compound having formula Va;

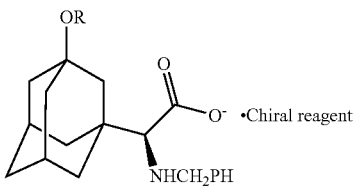

Formula Va wherein R is substituted or unsubstituted alkyl, substituted or unsubstituted aryl group;

iii) hydrolyzing the compound of formula Va in the presence of mineral acid to obtain a compound of formula VIa or its acid addition salts;

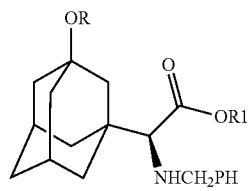

Formula VIa iv) reacting the compound of formula VIa with the compound 2-azabicyclo[3.1.0]hexane-3-carboxamide of formula VII or its acid addition salts;

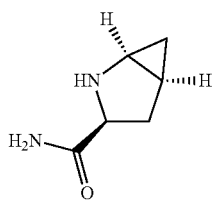

Formula VII in the presence of a coupling reagent and coupling additive to obtain a compound of formula VIIIa or its acid addition salts;

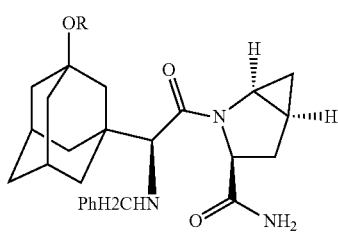

Formula VIIIa v) treating the compound of formula VIIIa or it acid addition salts with dehydrating agent in the presence of a base to obtain a compound of formula IXa or its acid addition salts;

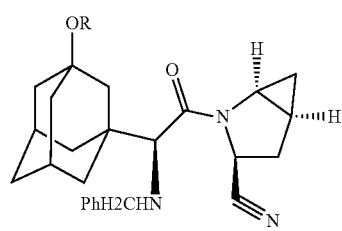

Formula IXa vi) catalytically reducing the compound of formula IXa or its acid addition salts in the presence of metal catalyst, to obtain the compound of formula X or its acid addition salts.

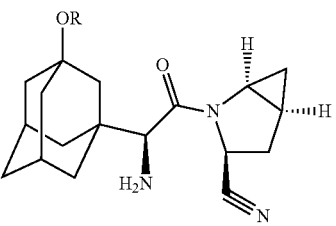

Formula X

The chiral reagent employed in step ii) is selected from the group of (S)-alpha methyl benzyl amine, (S)-phenyl ethyl amine, (S)-1,2 diamino propane, (S)-3-Hydroxy Pyrrolidine and (S)-phenyl alanine amide.

The coupling reagent employed in step iv) is selected, from the group of 1-ethyl-3-(3-dimethylaminopropyl) carbodiimide) HCl, N,N'-Dicyclohexylcarbodiimide, N,N,N',N'-Tetramethyl-O-(benzotriazol-1-yl)uronium tetrafluoroborate, O-(6-Chloro-1-hydrocibenzotriazol-1-yl)-1,1,3,3-tetramethyluronium tetrafluoroborate and benzotriazol-1-yl-oxytripyrrolidinophosphonium hexafluorophosphate.

The coupling additives employed in step iv) is selected from the group of hydroxybenzotriazole, hydroxybenzotriazole chloride and 1-hydroxy-7-azabenzotriazole.

The dehydrating reagent employed in step v) is selected from the group of trifluoroaceticanhydride, aceticannhydride, p-toulenesulfonyl chloride and bezenesulfonyl chloride.

The base employed in step v) is selected from the group of organic bases such as triethylamine, disopropylethylamine, pyridine, 2,6-dimethyl pyridine triethylamine and inorganic bases such as sodium hydroxide, potassium hydroxide, ammonium hydroxide, sodium bicarbonate, potassium bicarbonate, ammonium bicarbonate.

The metal catalyst employed in step vi) is selected from the group of Zn, Pt, Pd, Ni, Fe.

Suitable organic solvents employed to carry out the process included but are not limited to: alcohols such as methanol, ethanol, isopropyl alcohol, isobutyl alcohol, tertiary-butyl alcohol and the like; halogenated hydrocarbons such as dichloromethane, ethylene dichloride, chloroform and the like; ketones such as acetone, methyl isobutyl ketone and the like; nitriles such as acetonitrile, propionitrile and the like; ethers such as dimethyl ether, diethyl ether, diisopropyl ether, tetrahydrofuran, methyl tertiary-butyl ether and the like; esters such as ethyl acetate, n-propyl acetate, isopropyl acetate, n-butyl acetate, isobutyl acetate and the like; hydrocarbons such as hexane, benzene, xylene, toluene and the like and aprotic polar solvents such as dimethyl sulfoxide, N,N-dimethylformamide, N,N-dimethylacetamide and the like. Any solvent or mixture of solvents or their combination with water or any of the solvents from the classes mentioned above is acceptable.

The novel intermediates or its acid addition salts of the present invention may also prepared by methods known in the state of the art.

The following examples are provided to enable one skilled in the art to practice the invention and merely illustrate the process of the invention. However, it is not intended in any way to limit the scope of the present invention.

EXAMPLES

Example-1

Process for the Preparation of Bromo (tricyclo[3.3.1.1]acetic Acid

1-Adamantane acetic acid (100 g) was added portion wise to thionyl chloride (1.5 eq, 183.7 ml) at room temperature and the contents were maintained for 1.5 hrs under nitrogen atmosphere at the same temperature. Then N-Bromosuccinimide (1.5 eq, 137.4 g) was added portion wise at 25-30° C., heated the reaction contents to 70-75° C. and maintained for 3.0 hrs at same temperature. The reaction mixture was cooled to 0-5° C. The reaction mixture was quenched with water followed by the addition of THF. The reaction mixture was heated to 70-75° C. and stirred for 3.0 hrs at the same temperature. The reaction mixture was cooled down to 25-30° C., the pH of the reaction mixture was adjusted to 8-10 with saturated $Na_2CO_3$ solution then added 500 ml of methylene chloride. The pH of the reaction mass was adjusted to 2-3 with HCl, separated the methylene chloride layer. The methylene layer was washed with 20% $Na_2S_2O_3$ solution and distilled under vacuum below 45° C. The residue was mixed with acetonitrile, stirred for 1 hr at room temperature, filtered under vacuo and dried the resulting solid. Yield: 98 g (70%).

Example-2

Process for the Preparation of bromo (3-hydroxytricyclo[3.3.1.1]dec-1-yl)acetic Acid To a mixture of compound (100 g) from Example 1 and nitric acid (80 ml) at 0-10° C., con. sulphuric acid (600 ml) was added portion wise and stirred the resulting mixture for 10-12 hrs at 0-10° C. Water was added to the reaction mixture at 0-10° C. and the resulting mixture was stirred at same temperature for 2 hrs. The precipitate was filtered under vacuo, washed with water and dried. The crude product was mixed with acetonitrile and stirred at room temperature for 3 hrs. The contents were filtered and the resulting solid was washed with acetonitrile and dried. Yield: 78 g (75%).

Example-3

Process for the Preparation azido(3-hydroxytricyclo[3.3.1.1]dec-1-yl)acetic Acid Compound (50 g) from example-2 was dissolved in toluene (400 ml), followed by the addition of TBAB (0.1 eq, 5.56 g)), sodium azide (2 eq, 22.5 g) and water (200 ml) at 25-30° C. The resulting mixture was heated to 75-80° C. and maintained the reaction mass for 10-12. hrs at the same temperature. The reaction mixture was cooled to 0-10° C., quenched with water at the same temperature, the pH of the reaction mixture was adjusted to 2-3 with con. HCl. The resulting mixture was extracted with 500 ml of ethyl acetate and separated the ethyl acetate layer. The ethyl acetate layer was washed with water followed by sodium chloride solution, distilled under vacuum below 50° C. to afford crude product. The crude product was recrystallised using ethylacetate-heptane mixture to afford pure product. Yield: 30 g (87.5%)

Example-4

Process for the Preparation of Compound Having the Below Mentioned Structure

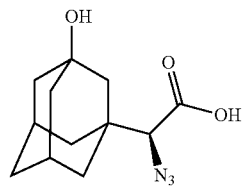 [SMILES: [N-]=[N+]=N[C@H](C(=O)O)C12CC3CC(CC(O)(C3)C1)C2]

Compound from example-3 was dissolved in 50 ml of acetone at 60-65° C. and S(−)-alpha methyl benzyl amine (1.0 eq) was added at the same temperature then maintained the reaction for 1.0 hr. The reaction mixture was cooled to 25-30° C., stirred the mass for 6.0 hrs at the same temperature and filtered the resulting solid. The solid was washed with acetone and dried. The dried compound was added to 2 M HCl solution at 25-30° C. and stirred for 2.0 hrs at the same temperature. The contents were filtered under vacuo and the resultant solid was washed with water and dried. Yield: 30%.

Example-4a

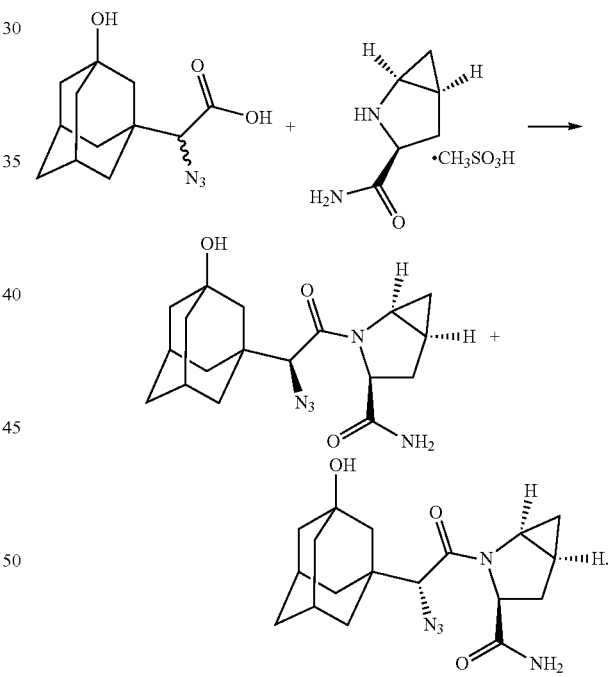

The Compound from example-(3) (10 g) was suspended in a mixture of ethylacetate (10 ml) and acetonitrile (23.5 ml). The compound of (1S,3S,5S)-2-Azabicyclo[3.1.0]hexane-3-carboxamide methane sulphonic acid (7.62 g) was added to the above suspension and followed by the addition of HOBT (20 g) under nitrogen. The reaction mixture was stirred at 25-30° C. for 10 minutes. The compound of 1-(3-Dimethylaminopropyl)-3-ethylcarbodiimide hydrochloride (23.2 g) was added to the reaction mixture at 25-30° C. and maintained for 10 minutes at the same temperature. A solution of DIPEA (17.1 g) was added to the reaction mixture at 0-5° C. over a period of 10-15 min under nitrogen. The temperature of the reaction mixture was raised to 25-30° C. and maintained at the same temperature for 3 hrs. After completion of the reaction, ethyl acetate (80 ml) and 1N Hydrochloric acid (10 ml Con HCL in 90 ml of water) was added to the reaction mixture at 25-30° C. and maintained for 15 min. The reaction mass was filtered and ethylacetate (50 ml) was added. The ethylacetate layer was separated. The aqueous layer was further extracted with ethylacetate (40 ml). The combined ethylacetate layers were washed with 20% potassium bicarbonate solution and distilled under vacuum to obtain concentrated liquid. The concentrated liquid was mixed with n-hexane and distilled under vacuum to get a residue. The residue was dissolved in n-hexane and stirred for 30 minutes at 25-30° C. The contents were filtered and the resultant solid was washed with n-hexane (10.0 ml) and dried at 50-55° C. in vacuum for 6 hrs. Yield: 95%.

Example-5

Process for the Preparation of Compound Having the Below Structure

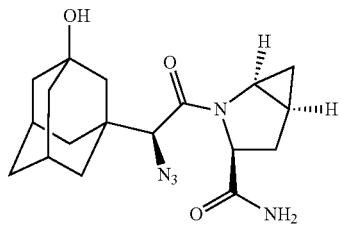 [SMILES: [N-]=[N+]=N[C@H](C(=O)N1[C@H](C(N)=O)C[C@@H]2C[C@@H]21)C12CC3CC(CC(O)(C3)C1)C2]

To a solution of Compound (10 g) from example-4 in a mixture of acetonitrile (25 ml) and ethylacetate (10 ml), (1S, 3S,5S)-2-Azabicyclo[3.1.0]hexane-3-carboxamide methane sulphonic acid (1.1 eq, 7.62 g), 1-(3-Dimethylaminopropyl)-3-ethylcarbodiimide hydrochloride (EDC.HCl) (1.1 eq, 23.2 g), hydroxyl benzotriazole (HOBT) (1.0 eq, 20 g) were added and the resulting mixture was stirred at room temperature for 15 min. The mixture was then cooled to 0-5° C. and a mixture of DIPEA (2.2 eq, 17.1 g), ethylacetate (10 ml) and acetonitrile (25 ml) was added slowly at the same temperature and maintained the reaction mass for 1 hr at 0-5° C., then at room temperature for 3 hrs. The reaction mixture was mixed with ethylacetate and 1N Hydrochloric acid and maintained for 15 min. The resulting precipitate was filtered and washed the solid with ethylacetate. The ethyl acetate layer was separated. The aqueous layer was extracted with ethyl acetate. The combined ethyl acetate layers were washed twice with 20% potassium bicarbonate solution followed by washings with saturated sodium chloride solution and distilled under vacuo to afford the crude product. The crude product was mixed with n-hexane, stirred for 30 minutes at room temperature and filtered under vacuo, the resultant solid was washed with hexane and dried. Yield: 76%.

Example-6

Process for the Preparation of Compound Having the Below Structure

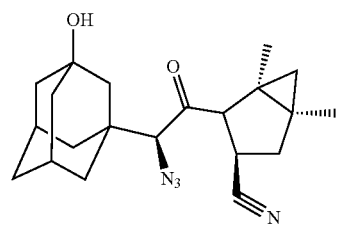 [SMILES: C[C@]12C[C@@H](C#N)C(C(=O)[C@@H](N=[N+]=[N-])C34CC5CC(CC(O)(C5)C3)C4)[C@@]1(C)C2]

Compound from example-5 (10 g) was dissolved in ethylacetate (100 ml) followed by the addition of pyridine (5.0 eq, 11.2 g). The reaction mixture was cooled to 0-5° C., then trifluoroacetic anhydride (3.0 eq, 9.6 ml) was added and stirred for 1-1.5 hrs at the same temperature. The reaction mixture was distilled under vacuum below 50° C. and dissolved in 100 ml of methanol. Potassium carbonate solution (10 ml) was added to the reaction mixture at 25-30° C. and stirred the reaction mass at 40-45° C. for 3 hrs. The reaction mixture was distilled below 50° C. under vacuum to get a residue. The residue was mixed with water, and the pH was adjusted to 7, then extracted with ethylacetate. The ethylacetate layer was washed with sodium bicarbonate solution followed by saturated sodium chloride solution and distilled under vacuum below at 45° C. to afford crude product. The crude product was recrystallised from mixture of isopropyl alcohol and water to obtain pure product. Yield: 68%.

Example-7

Process for the Preparation of Saxagliptin Hydrochloride

Compound from example-6 was dissolved in 50 ml of methanol followed by the addition of water, Zinc powder (1.1 eq) and ammonium chloride (2.0 eq) at 25-30° C., and maintained for 2.0 hrs at same temperature. The reaction mass was filtered and washed with 55 ml of methanol. The filtrate was distilled under vacuum below 50° C. and the residue was mixed in ethyl acetate. Concentrated HCl was added to reaction mixture and maintained for 4.0 hrs at 25-30° C. The resulting precipitate was filtered under vacuo, washed with ethylacetate and dried to obtain the title compound Saxagliptin hydrochloride. Yield: 73%.

Example-8

Process for the Preparation of Saxagliptin Monohydrate

Compound from example-7 was dissolved in water and the pH was adjusted to 9-10 with sodium carbonate solution at 25-30° C., then 140 ml of methylene chloride was added, stirred the mass for 30 minutes at the same temperature and separated the methylene chloride layer. The aqueous layer was further extracted with methylene chloride. The combined organic layers were distilled and the resulting residue was dissolved in 35 ml of ethyl acetate and treated with purified water. The resulting slurry was stirred for 4.0 hrs and filtered under vacuo. The resulting solid was dried at below 40° C. Yield: 74%.

Example-9

Process for the Preparation of the Compound Having the Below Structure

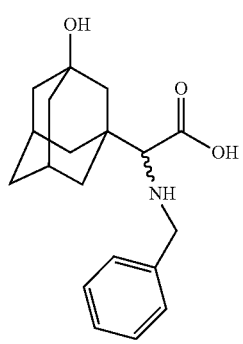 [SMILES: O=C(O)C(NCc1ccccc1)C12CC3CC(CC(O)(C3)C1)C2]

The compound from example-2 was added to benzylamine (6 eq) and heated at 110° C. and maintained the reaction for 3.0 hrs at the same temperature. The reaction mixture was cooled to 25-30° C. and water was added. The pH of the reaction mixture was adjusted to 7.0-8.0 with dilute HCl and filtered the resulting solid. Yield: 82%

Example-10

Process for the Preparation of the Compound Having the Below Mentioned Structure

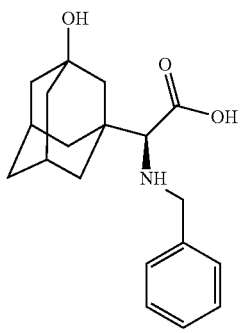 [SMILES: O=C(O)[C@@H](NCc1ccccc1)C12CC3CC(CC(O)(C3)C1)C2]

The compound from example-9, was dissolved in 50 ml of methanol, heated up to 60-65° C., S (−) alpha methyl benzyl amine (1.0 eq) was added at the same temperature and stirred for 1 hr at same temperature. The reaction mixture was cooled to 25-30° C. and maintained for 6.0 hrs at same temperature. The reaction mixture was filtered to obtain a solid and washed with methanol and dried. The solid was added to 2 M HCl solution at 25-30° C. and stirred for 1.0 hr at the same temperature. The resulting precipitate was filtered under vacuo and dried. Yield: 35%

Example-11

Process for the Preparation of the Compound Having the Below Mentioned Structure

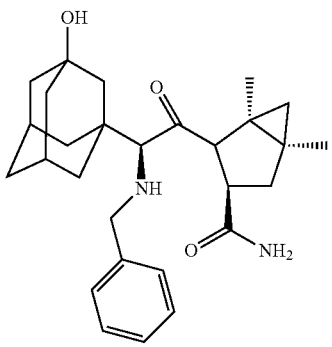 [SMILES: C[C@]12C[C@@H](C(N)=O)C(C(=O)[C@@H](NCc3ccccc3)C34CC5CC(CC(O)(C5)C3)C4)[C@@]1(C)C2]

To a solution of Compound (10 g) from example-10 in a mixture of acetonitrile (25 ml) and ethylacetate (10 ml), (1S, 3S,5S)-2-Azabicyclo[3.1.0]hexane-3-carboxamide methane sulphonic acid (1.1 eq, 7.62 g), 1-(3-Dimethylaminopropyl)-3-ethylcarbodiimide hydrochloride (EDC.HCl) (1.1 eq, 23.2 g), hydroxyl benzotriazole (HOBT) (1.0 eq., 20 g)) were added and the resulting mixture was stirred at room temperature for 15 minutes. The mixture was then cooled to 0-5° C. and a mixture of DIPEA (2.2 eq, 17.1 g), ethylacetate (10 ml) and acetonitrile (25 ml) was added slowly at the same temperature and maintained the reaction mass for 1 hr at 0-5° C., then at room temperature for 3 hrs. The reaction mixture was mixed with ethylacetate and 1N Hydrochloric acid and maintained for 15 minutes. The resulting precipitate was filtered and washed the solid with ethylacetate. The organic layer of the filtrate was separated and the aqueous layer was extracted with ethyl acetate. The combined ethyl acetate layers were washed twice with 20% potassium bicarbonate solution followed by washings with saturated sodium chloride solution and distilled under vacuo to afford the crude product. The crude product was mixed with n-hexane, stirred for 30 minutes at room temperature and filtered under vacuo. The resultant solid was washed with hexane and dried. Yield: 76%.

Example-12

Process for the Preparation of the Compound Having the Below Mentioned Structure

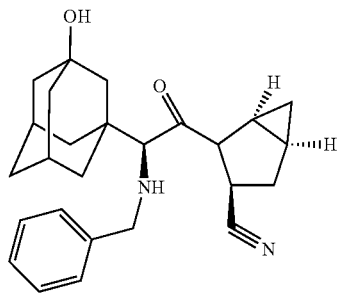 [SMILES: N#C[C@@H]1C[C@@H]2C[C@@H]2C1C(=O)[C@@H](NCc1ccccc1)C12CC3CC(CC(O)(C3)C1)C2]

Compound from example-11 (10 g) was dissolved in ethylacetate (100 ml) followed by the addition of pyridine (5.0 eq, 11.2 g), then the mixture was cooled to 0-5° C. Trifluoroacetic anhydride (3.0 eq, 9.6 ml) was added to the resultant mixture and stirred for 1-1.5 hrs at the same temperature. The reaction mixture was distilled under vacuum below 50° C. and the concentrate was dissolved in 100 ml of methanol. Potassium carbonate solution (10 ml) was added to the reaction mixture at 25-30° C., stirred the at 40-45° C. for 3 hrs and distilled methanol below 50° C. under vacuum. The residue was mixed with water, the pH was adjusted to 7 and extracted with ethylacetate. The ethylacetate layer was washed with sodium bicarbonate solution followed by saturated sodium chloride solution and distilled under vacuum below at 45° C. to afford crude product. The crude product was recrystallised from mixture of water and isopropyl alcohol to obtain pure product. Yield: 68%.

Example-13

Process for the Preparation of the Saxagliptin Hydrochloride

Compound from Example-12 was dissolved in methanol 0.05 mol, followed by the added 10% Pd—C (10% w/w) at 25-30° C. and maintained the reaction for 2 hrs at same temperature. The reaction mixture was filtered over hyflow and washed with 25 ml of methanol. The filtrate was distilled under vacuum below at 50° C. and the residue was dissolved in ethyl acetate. HCl was added to resultant reaction mixture and stirred for 4 hrs at 25-30° C. The solid obtained was filtered. Yield: 80%.

Example-14

Process for the Preparation of the Saxagliptin Monohydrate

Compound from example-13 was taken in to water and the pH of the reaction mixture was adjusted to 9-10 with sodium carbonate solution at 25-30° C. Methylene chloride 10 ml was added to reaction mixture and stirred the mass for 30 minutes at the same temperature. The methylene chloride layer was separated. The methylene chloride layer was distilled and the residue was dissolved in ethyl acetate. The purified water was added to the above contents and stirred for 4 hrs at the same temperature. The resulting solid was filtered. Yield: 70%.

Example-15

Process for the Preparation of Saxagliptin Monohydrate

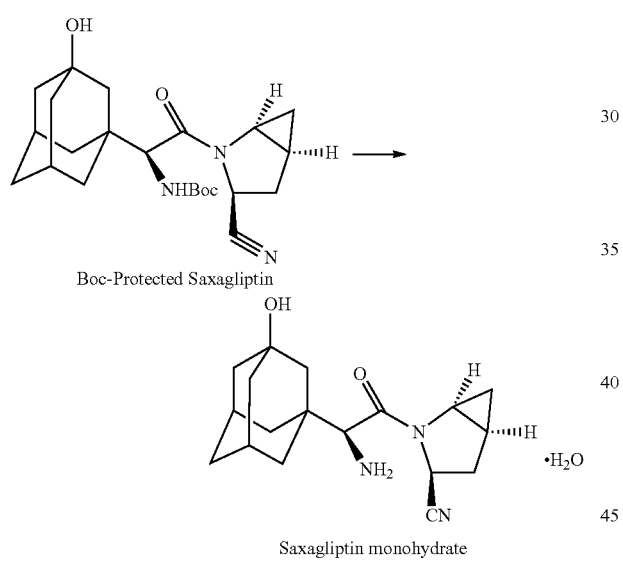

The compound of Boc protected (amino group protected by Di-tert-butyl dicarbonate group) saxagliptin (5.0 g gm) was dissolved in methylene chloride (40 ml); and the concentrated hydrochloric acid (4 ml) was added to the above solution. The reaction mixture was stirred for 4 hrs at 25-30° C. After the completion of the reaction, purified water (40 ml) was added to the reaction mixture at 25-30° C. and the pH was adjusted to 9-10 by the addition of potassium carbonate at the same temperature. Methylene chloride (20 ml) was added to the reaction mixture and stirred. The methylene chloride layer was separated and distilled under vacuum. The resulting residue was mixed with ethylacetate (25 ml) and treated with purified water. The contents were stirred, the resultant solid was filtered under vacuum and dried at 50-55° C. for 6 hrs. Yield: 75%.

We claim:
1. A process for the preparation of the saxagliptin comprising the steps of:

i) reacting the compound of formula III or its acid addition salts

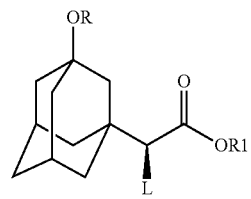

Formula III wherein R and R1 independently is H or C1-C6 substituted or unsubstituted alkyl group; L is a halogen or leaving group;

with alkali metal azide in the presence of a phase transfer catalyst to obtain a compound of formula IV or its acid addition salts

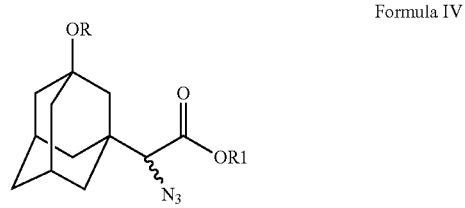

Formula IV wherein R and R1 independently is H or C1-C6 substituted or unsubstituted alkyl group;

ii) treating the compound of formula IV with chiral reagent to obtain the compound of formula V;

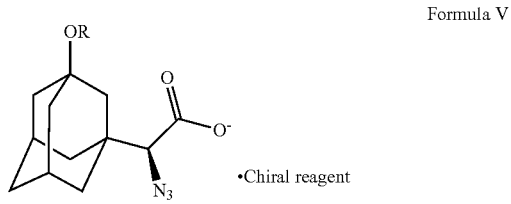

Formula V iii) hydrolysis of the compound of formula V by employing mineral acid to obtain a compound of formula VI

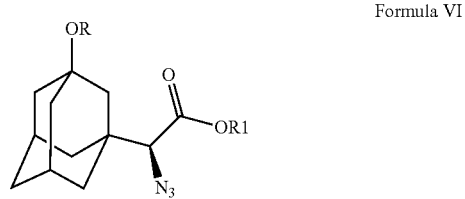

Formula VI wherein R and R1 independently is H or C1-C6 substituted or unsubstituted alkyl group;

iv) reacting the compound of formula VI with the compound 2-azabicyclo[3.1.0]hexane-3-carboxamide of formula VII or its acid addition salts

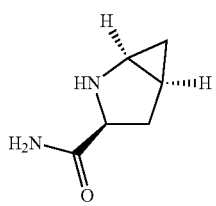

Formula VII in the presence of a coupling reagent and coupling additives to obtain a compound of formula VIII or its acid addition salts;

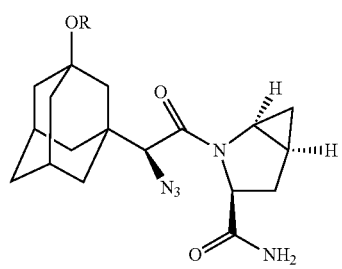

Formula VIII v) dehydrating the compound of formula VIII or its acid addition salts in the presence of a dehydrating reagent and base to obtain a compound of formula IX or its acid addition salts;

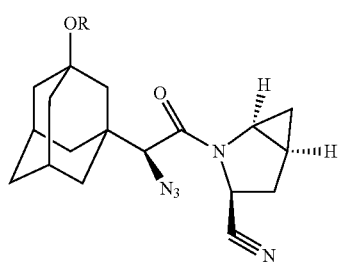

Formula IX vi) reducing the compound of formula IX or its acid addition salts in the presence of a metal catalyst to obtain compound of formula X or its acid addition salts

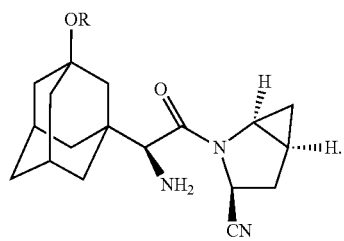

Formula X

2. The process according to claim 1, wherein the alkali metal azide employed is selected from the group consisting of potassium azide, rubidium azide, sodium azide and cesium azide.

3. The process according to claim 1, wherein the phase transfer catalyst employed is selected from the group of tetrabutyl ammonium chloride and tetrabutyl ammonium hydrogen sulphate.

4. The process according to claim 1, wherein the chiral reagent employed is selected from the group of (S)-alpha methyl benzyl amine, (S)-phenyl ethyl amine, (S)-1,2 diamino propane, (S)-3-hydroxy pyrrolidine and (S)-phenyl alanine amide.

5. The process according to claim 1, wherein the coupling reagent employed is selected from the group of 1-ethyl-3-(3-dimethylaminopropyl) carbodiimide) HCl, N,N'-dicyclohexylcarbodiimide, N,N,N',N'-tetramethyl-O-(benzothazol-1-yl)uronium tetrafluoroborate, O-(6-Chloro-1-hydrocibenzotriazol-1-yl)-1,1,3,3-tetramethyluronium tetrafluoroborate and benzotriazol-1-yl-oxytripyrrolidinophosphonium hexafluorophosphate.

6. The process according to claim 1, wherein the coupling additives employed is selected from the group of hydroxybenzotriazole, hydroxybenzotriazole chloride and 1-hydroxy-7-azabenzotriazole.

7. The process according to claim 1, wherein the dehydrating reagent employed is selected from the group of trifluoroaceticannhydride, aceticannhydride, p-toulenesulfonyl chloride and bezenesulfonyl chloride trifluoroaceticannhydride.

8. The process according to claim 1, wherein the base employed is selected from the group of organic bases such as triethylamine, disopropylethylamine, pyridine, 2,6-dimethyl pyridine triethylamine and inorganic bases such as sodium hydroxide, potassium hydroxide, ammonium hydroxide, sodium bicarbonate, potassium bicarbonate, ammonium bicarbonate.

9. The process according to claim 1, wherein the metal catalyst is selected from Zn, Pd, Pt, Ni, and Fe.

10. A process for the preparation of Saxagliptin comprising the steps of:
i) reducing the compound of formula IX or its acid addition salts

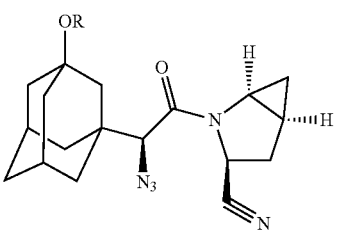

Formula IX in the presence of a metal catalyst to obtain the compound of formula X or its acid addition salts.

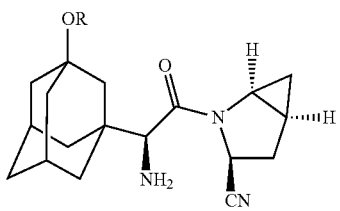

Formula X

11. The process according to claim 10, wherein the metal catalyst is selected from the Zn, Pd, Pt, Ni, and Fe.

12. A process for the preparation of Saxagliptin comprising the steps of:
i) treating the compound of formula VIII or its acid addition salts,

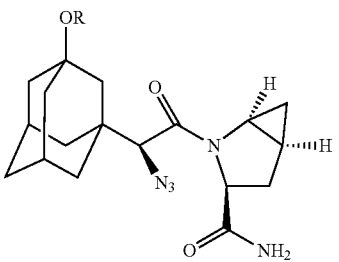

Formula VIII with palladium catalyst to obtain the compound of formula A or its acid addition salts;

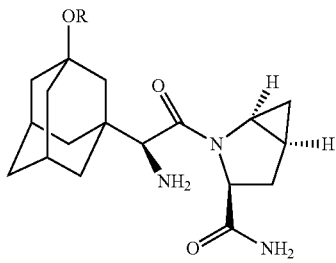

Formula A ii) treating the compound of formula A or its acid addition salts with N-protecting reagents to obtain the compound of formula B or its acid addition salts

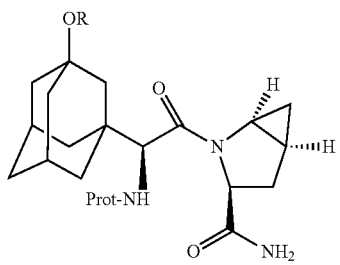

Formula B wherein Prot is N-protecting group;

iii) treating the compound of formula B or its acid addition salts with dehydrating reagent and base to obtain a compound of formula C or its acid addition salts;

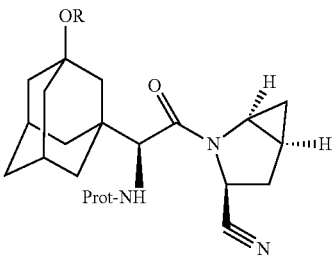

Formula C iv) treating the compound of formula C or acid addition salts with mineral acid to obtain the Saxagliptin or its acid addition salts.

13. The process according to claim 12, wherein the N-protecting reagents employed is selected from the group of carbobenzyloxy, p-methoxybenzyl carbonyl, tert-butyloxycarbonyl, 9-fluorenylmethyloxycarbonyl, benzoyl, benzyl, carbamate group, p-methoxybenzyl and 3,4-dimethoxybenzyl.

14. The process according to claim 12 wherein the dehydrating reagent employed is selected from the group of trifluoroaceticannhydride, aceticannhydride, p-toulenesulfonyl chloride and bezenesulfonyl chloride trifluoroaceticannhydride.

15. The process according to the claim 12, wherein the base employed is selected from the group of organic bases such as triethylamine, disopropylethylamine, pyridine, 2,6-dimethyl pyridine triethylamine and inorganic bases such as sodium hydroxide, potassium hydroxide, ammonium hydroxide, sodium bicarbonate, potassium bicarbonate, ammonium bicarbonate.

\* \* \* \* \*